United States Patent [19]
Cole et al.

[11] Patent Number: 5,660,989
[45] Date of Patent: Aug. 26, 1997

[54] DNA POLYMERASE EXTENSION ASSAY FOR INFLUENZA VIRUS ENDONUCLEASE

[75] Inventors: James L. Cole, Doylestown; Lawrence C. Kuo, Solebury; David B. Olsen, Lansdale, all of Pa.

[73] Assignee: Merck & Co., Inc., Rahway, N.J.

[21] Appl. No.: 487,759

[22] Filed: Jun. 7, 1995

[51] Int. Cl.[6] .................................................. C12Q 1/68
[52] U.S. Cl. ........................ 435/6; 536/23.1; 536/24.3
[58] Field of Search ............................. 435/6; 536/24.3, 536/23.1

[56] References Cited

PUBLICATIONS

Plotch et al. Cell 23:847–858 (1981).
Kuppuswamy et al. PNAS 88:1143–1147 (1991).
Tomassini et al. Antimicrobial Agents and Chemotherapy 38(12):2827–2837 (1994).
The Amersham Catalog p. 40 (1993).
James M. Clark, "Laboratory of Molecular Genetics, National Institute of Environmental Health Sciences", Research Triangle Park, NC 27709, USA. vol. 16 No. 20, 1988.
Stephen J. Plotch, et al. "A Unique Cap(m7GpppXm)–Dependent Influenza Virion Endonuclease Cleaves Capped RNAs to Generate the Primers That Initiate Viral RNA Transcription", Cell, vol. 23, 847–858, Mar. 1981.

Stephen J. Plotch, et al. "Influenza Virion Transcriptase: Synthesis In Vitro of Large, Polyadenylic Acid–Containing Complementary RNA" Journal of Virology, Jan. 1977, pp. 24–34, vol. 21, No. 1.

Stanley Tabor et al. "Selective Inactivation of the Exonuclease Activity of Bacteriophage T7 DNA Polymerase by in Vitro Mutagenesis*" The Journal of Biological Chemistry, vol. 264, No. 11, Issue Apr. 15, pp. 6447–6458, 1989.

J. Tomassini, et al. "Inhibition of Cap(m7GpppXm)–Dependent Endonuclease of Influenza Virus by 4–Substituted 2,4–Dioxobutanoic Acid Compounds" Antimicrobial Agents and Chemotherapy, Dec. 1994, pp. 2827–2837.

*Primary Examiner*—W. Gary Jones
*Assistant Examiner*—Ethan C. Whisenant
*Attorney, Agent, or Firm*—Joanne M. Giesser; Jack L. Tribble

[57] ABSTRACT

An assay for the influenza virus endonuclease has been developed which involves DNA polymerase-catalyzed extension of the viral endonuclease cleavage product using labeled nucleotides and a DNA template containing a 3' region complementary to the product joined to a 5' region consisting of repeated residues. The DNA polymerase coupled assay does not involve gel electrophoretic separation and is amenable to high volume screening of potential inhibitors. Another key feature of the assay is that it is sensitive enough to detect 200 attomoles of product.

25 Claims, 4 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear (iii) HYPOTHETICAL: NO (iv) ANTI-SENSE: NO (xi) SEQUENCE DESCRIPTION: SEQ ID NO:1:

GUUUUUAUUU UUAAUUUUC                                                                       19

(2) INFORMATION FOR SEQ ID NO:2:

(i) SEQUENCE CHARACTERISTICS:
                (A) LENGTH: 13 base pairs
                (B) TYPE: nucleic acid
                (C) STRANDEDNESS: single
                (D) TOPOLOGY: linear (iii) HYPOTHETICAL: NO (iv) ANTI-SENSE: NO (xi) SEQUENCE DESCRIPTION: SEQ ID NO:2:

ACACUUGCUU UUG                                                                             13

(2) INFORMATION FOR SEQ ID NO:3:

(i) SEQUENCE CHARACTERISTICS:
                (A) LENGTH: 13 base pairs
                (B) TYPE: nucleic acid
                (C) STRANDEDNESS: single
                (D) TOPOLOGY: linear (iii) HYPOTHETICAL: NO (iv) ANTI-SENSE: NO (xi) SEQUENCE DESCRIPTION: SEQ ID NO:3:

GTTTTTATTT TTA                                                                             13

(2) INFORMATION FOR SEQ ID NO:4:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (iii) HYPOTHETICAL: NO (iv) ANTI-SENSE: NO (xi) SEQUENCE DESCRIPTION: SEQ ID NO:4:

CCCCCCCCC TAAAATAAA AAC                                                                    23

(2) INFORMATION FOR SEQ ID NO:5:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (iii) HYPOTHETICAL: NO (iv) ANTI-SENSE: NO (xi) SEQUENCE DESCRIPTION: SEQ ID NO:5:

CCCCCCCCC TTAAAAATAA AAAC                                                                  24

DNA POLYMERASE EXTENSION ASSAY FOR INFLUENZA VIRUS ENDONUCLEASE

FIELD OF THE INVENTION

This invention relates to a novel sensitive assay to detect and quantify the presence of influenza virus endonuclease and inhibitors of influenza virus endonuclease activity.

BACKGROUND OF THE INVENTION

The influenza A virus genome consists of eight negative-sense single-stranded RNA segments. Synthesis of viral mRNA is catalyzed by a viral-encoded RNA-dependent RNA polymerase (E.C. 2.7.7.48). Influenza virus transcription is initiated by a mechanism in which primers are generated by cleaving host cell transcripts 10–13 nucleotides from their 5' cap structure. The cleavage and priming reactions are dependent on the transcript possessing a cap-1 structure containing a 7-methylated terminal G and a 2'-O-methylated penultimate purine base (7mGpppRm). The influenza endonuclease represents an attractive target for development of antiviral agents, and recently both small molecule (Tomassini et al, 1994 AntiMicrob. Agents and Chemo. 38:2827–2837) and oligonucleotide inhibitors (Chung et al 1994 Proc. Natl. Acad. Sci. USA 91:2372–2376) have been described.

Screening for potential inhibitors of the influenza endonuclease has been hampered, however, by the lack of a suitable assay method. An ideal assay system should have: a) high throughput; b) the ability to distinguish influenza endonuclease-catalyzed cleavage from nonspecific RNA cleavage; and c) high sensitivity. Previous endonuclease assays involved the use of polyacrylamide gel electrophoresis to separate product from substrate (Plotch et al, 1981 Cell 23: 847–858) which is not convenient for processing large numbers of samples. Assays have also been described for the overall influenza transcriptase reaction which may be capable of detecting inhibition of the endonuclease (Plotch et al, 1977 J. Virol. 21:24–34.). However, the overall reaction is a complex, multistep process in which cleavage may not be rate-limiting and endonuclease inhibitors may be missed.

DETAILED DESCRIPTION OF THE INVENTION

This invention is directed to a novel, accurate, sensitive, rapid assay which is specific for influenza virus endonuclease activity. This invention comprises a method detecting the influenza endonuclease activity of a sample comprising:

A) adding an influenza endonuclease substrate to a sample whose influenza endonuclease activity is to be assayed, to generate an RNA product;

B) hybridizing the RNA product with a DNA template, said DNA template comprising a first segment substantially complementary to the RNA product and a 5'-template extension region attached to the first segment, said template extension region comprising at least one nucleotide, under hybridization conditions to form a RNA:DNA heteroduplex;

C) adding labeled mononucleotide which is complementary to the second segment of the DNA template;

D) adding a DNA polymerase to the heteroduplex under conditions permitting the DNA polymerase to catalyze the addition of the labeled mononucleotide to the 3'-end of the RNA product to produce a labeled hybrid polymerase product; and E) measuring the amount of labeled hybrid polymerase product as a measure of the amount of influenza endonuclease activity of the sample.

In accordance with this invention, the sample to be analyzed may contain an unknown quantity of influenza endonuclease. In this embodiment of the invention, the amount of influenza endonuclease present in the sample may be quantified. In an alternative preferred embodiment, the sample may contain a known amount of influenza endonuclease and a molecule whose influenza endonuclease inhibitory activity is to be determined. The amount of labeled hybrid polymerase product is compared to the amount of labeled hybrid polymerase product produced by a control sample where no inhibitors were present, and the degree of inhibitory activity present in the sample can be determined.

To determine the amount of labeled hybrid polymerase product present, any detection method may be employed. A preferred method is to pass the sample containing labeled hybrid polymerase product and excess labeled mononucleotide through a filter which traps the labeled hybrid polymerase product and determining the amount of labeled hybrid polymerase product which has been trapped on the filter.

DEFINITIONS

Figure 1:
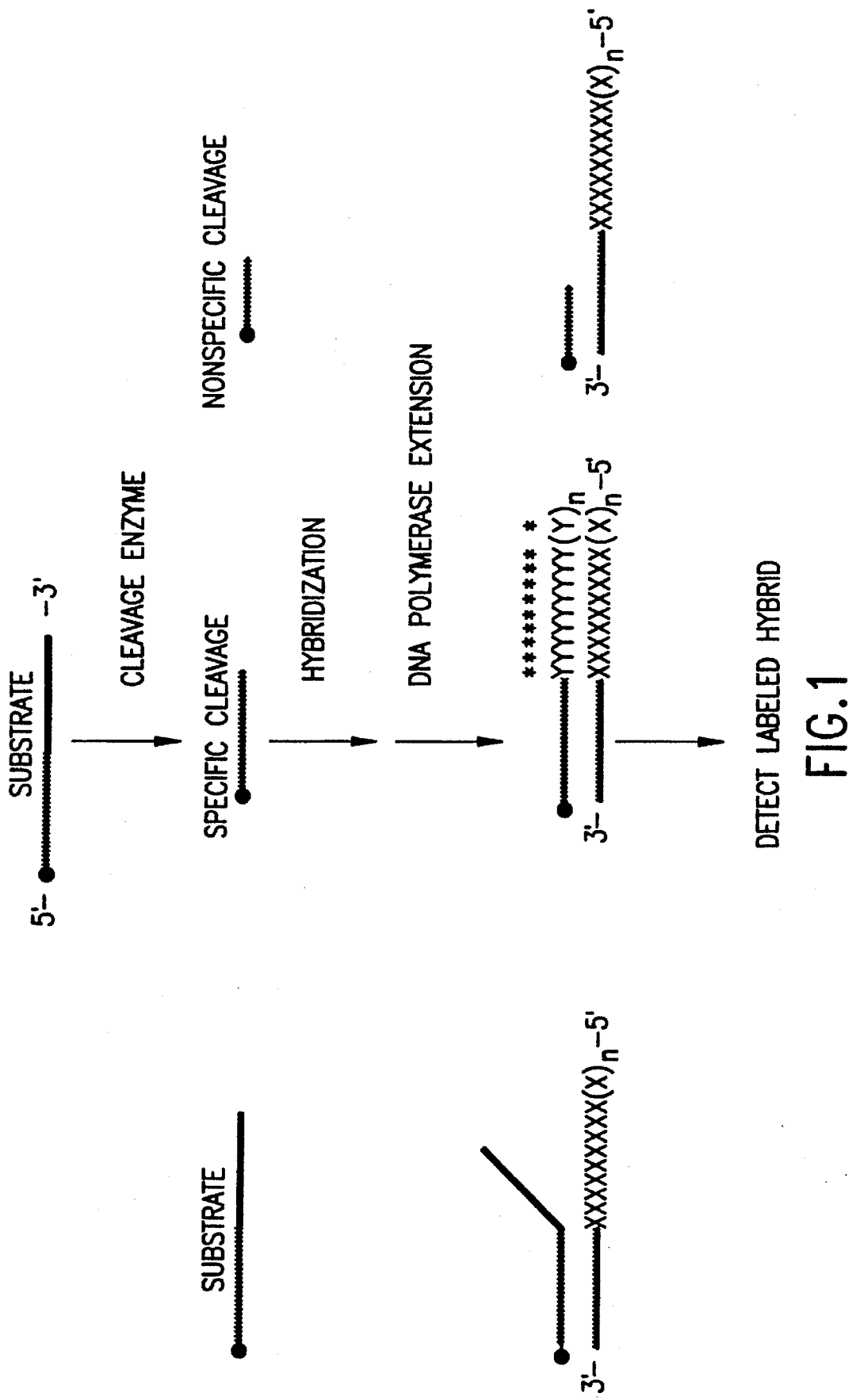
FIG. 1 is a flowchart illustrating the DNA polymerase amplification assay for influenza virus endonuclease.

Throughout the specification and claims the following definitions shall apply:

"nt" is the abbreviation for nucleotide.

"AlMV" is the abbreviation for Alfalfa Mosaic Virus.

"Substantially complementary" means that there is sufficient complementarity so that under the experimental conditions employed, the 3'-region of the RNA primer will hybridize with the DNA template strand such that the resulting heteroduplex is capable of serving as a substrate for a DNA polymerase. "Substantially complementary" further requires that there is sufficient complementarity so that a heteroduplex can form and that the heteroduplex has sufficient stability so that its melting temperature is greater than the freezing point of the solvent system.

"Oligonucleotide" is at least two nucleotides in length.

"Substantially repeated" means that the oligo-nucleotide is made up of at least 80% of the same base, preferably at least 90% of the same base, and even more preferably at least 95% of the same base.

"Derived from AlMV" means that the oligonucleotide is at least 80% homologous to the 5'-end of the AlMV 4 RNA, and is able to act as a substrate of influenza endonuclease, i.e., it can be cleaved by influenza endonuclease.

The substrate can be any 5'-capped RNA which is cleaved by the influenza endonuclease. Preferably, the endonuclease substrate is derived from the 5' end of the AlMV 4 RNA, which has been previously demonstrated to be a substrate for the influenza endonuclease and is cleaved at nucleotide A13. In a preferred embodiment of this invention, the influenza endonuclease substrate is a 19 nt 5'-capped RNA substrate which is cleaved by the influenza endonuclease, generating a 13 nt product. The 19 nt 5'-capped RNA substrate may be made by treating a 19 nt RNA containing a 5'-triphosphate with a guanylyltransferase. The capped RNA substrate may be obtained according to co-pending U.S. Ser. No. 08/480,068, (Attorney Docket No. 19406) and co-pending U.S. Ser. No. 08/487,760, (Attorney Docket No. 19398), both filed herewith, each of which is hereby incorporated by reference. Guanylyltransferases are well known and may be obtained commercially; for example, Vaccinia virus guanylyltransferase may be purchased from Bethesda Research Laboratories, Gaithersburg, Md.

This 13 nt RNA product resulting from cleavage of the 19 nt product by the influenza endonuclease is then used as a primer for a DNA polymerase-catalyzed extension reaction. In order for the polymerase extension reaction to proceed, a DNA template is required. The DNA template is a two-part molecule: it contains a 3'-region which is substantially complementary to the 13 nt RNA primer, joined to a template 5'-extension region. Although in theory the 5'-extension region may be made from any desired nucleotides, it is preferred that they be substantially repeated nucleotides, and that the nucleotides present in the extension region not be present in the 3'-complementary region of the DNA in order to achieve specificity for product cleaved at the correct position. In the most preferred embodiment, the 5'-extension region made up of repeated nucleotides. If the 5'-extension region is not made from substantially repeated nucleotides, then there may be specificity problems with the assay, unless the extension region is quite long to amplify the signal of the correct cleavage product relative to non-specific products.

There is no particular limit as to the length of the extension region; it may be as short as a single nucleotide or as long as existing synthesis methods permit (up to or exceeding 50 nucleotides). In preferred embodiments, the 5'-extension region is at least one nucleotide residue in length, and is more preferably at least about 10 residues in length. Thus, the template extension region should preferably be a poly-dC, a poly-dG, a poly-dA, or a poly-dT region. In one preferred embodiment of this invention, the template extension region is a poly-dC residue 10 nt in length.

During the DNA polymerase-catalyzed extension reaction, the 13 nt RNA product will be extended in length by labeled mononucleotides which are complementary to the nucleotides present in the DNA template extension region. For example, if the template extension region is a 10 residue poly-C, the 13 nt RNA product will be extended 10 bases by a labeled poly-G sequence. While any type of label which is conventionally used in the nucleotide assay arts may be used to label the nucleotides which will be incorporated into the product extension region of the RNA, such as fluorescent or absorption labels, it is preferred to use a radiolabel. In a preferred embodiment, the product extension region is poly-a-$^{32}$p labeled dGMP (as shown in FIG. 1).

Additionally, to prevent a polymerase-catalyzed extension from occurring on the 3'-OH end of the template, the 3'-OH of the primer is preferably blocked. Numerous blocking materials are known and suitable, and include cordycepin (3'-deoxyadenosine) and other 3'-bases without a 3'-OH moiety, and other blocking moieties. In one embodiment of this invention, the Y-OH is blocked with a (3-amino-2-hydroxy)-propoxyphosphoryl moiety. In another embodiment of the invention, the 3'-OH is blocked by the introduction of a 3'-3'-A-5' linkage. While it is possible to run an assay of this invention without blocking the 3'-OH of the primer, blocking the 3'-OH end helps to prevent background signal and thus helps to increase the sensitivity of the assay.

Numerous DNA polymerase enzymes are known and may be used in the DNA polymerase reaction step of this invention. In a preferred embodiment, Sequenase® Version 2, a mutant of bacteriophage T7 DNA polymerase (obtained from United States Biochemicals, Cleveland, Ohio) in which the 3' to 5' exonuclease activity is abolished by in vitro mutagenesis (Tabor et al, 1989 J. Biol. Chem 264:6447–6458) is the DNA polymerase. This polymerase is preferred because it is able to use oligoribonucleotides as primers, it replicates with high fidelity and does not have a 3' to 5' "proofreading" activity.

Depending on the type of label used, detection of the labeled hybrid polymerase product may be achieved by any appropriate means. Generally this may include a step of separating labeled mononucleotide from labeled hybrid polymerase product. In a preferred embodiment, detection is achieved by filtering the sample mixture (which at this point in the assay method, contains the labeled hybrid polymerase product and excess labeled mononucleotide) through a nylon membrane. The unincorporated excess labeled mononucleotides flow through the membrane while the labeled hybrid polymerase reaction product is captured. If the label was a radiolabel, then the amount of radioactivity bound to the filter may be quantitated using a phosphorimager or by a plate reading scintillation counter.

This assay has distinct advantages over the prior art assays in that it does not involve an electrophoresis step and may be run in 96-well microtiter plate format. Other key advantages of the assay of this invention are that it monitors the substrate cleavage reaction only at the correct position in the sequence, thereby discriminating against nonspecific RNA cleavage products. Also importantly, this assay is sensitive enough to detect 200 attomoles ($2 \times 10^{-16}$ moles) of product generated in a typical cleavage reaction.

The specificity of the assay is achieved through the choice of the DNA template and the high fidelity of the T7 DNA Sequenase® polymerase. Under the conditions of a typical reaction more than 90% of the substrate is not cleaved, but this does not interfere with the specificity of the assay because the uncleaved RNA substrate does not serve as a primer for polymerization, since the 3' end cannot base-pair to the template. In addition, nonspecific cleavage products with 3' termini other than A13 will not be extended. Although these shorter sequences may hybridize with the template, they are not extended by the DNA polymerase because this reaction would require dATP or dTTP, which are not present in the reaction mixture in the case where the template extension region consists of poly-dC.

The polymerase extension reaction is dependent on hybridization of the RNA primer onto the DNA template.

Therefore, for effective hybridization of the RNA primer to the DNA template, polymerase extension reactions are preferably carried out at least 10° C. below the melting temperature of the DNA:RNA complex. A typical preferred reaction temperature is 0° C. for a primer:template complex with a melting temperature of 14° C.

Figures 2A, 2B:
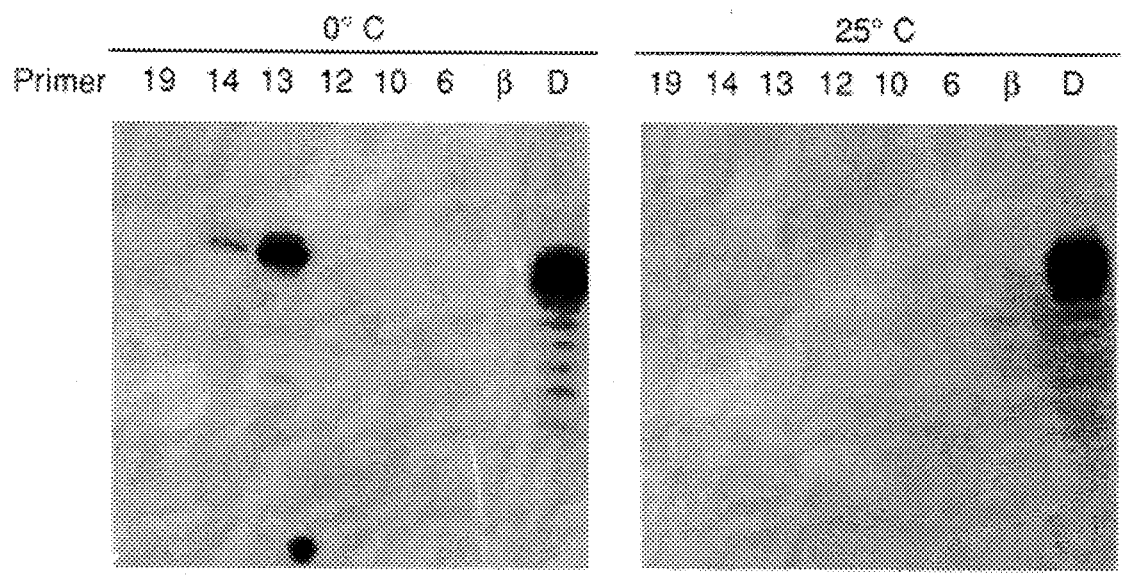
FIG. 2 is a photograph of a phosphorimager scan of a 20% acrylamide 8M urea polyacrylamide gel demonstrating the effects of primer length and temperature on polymerase-catalyzed extension reactions. The lane labeled 19 corresponds to an uncapped RNA primer (19 nt) with the sequence of the AlMV substrate (5'-GUUUUUAUU-UUUAAUUUUC-3') (SEQ.ID.NO.:1); lanes labeled 14-6 correspond to RNA primers of the indicated length derived from 3' deletions of the 19 nt primer. The lane labeled b corresponds to a 13 nt RNA derived from the 5' end of b-globin mRNA (5'-ACACUUGCUUUUG-3') (SEQ.ID.NO.:2). The lane labeled D corresponds to a 13 nt DNA with the AlMV primer sequence (5'-GTTTTTATTTTTA-3') (SEQ.ID.NO.:3).

FIG. 2 illustrates the specificity of the Sequenase®-catalyzed extension reaction and the effects of temperature. Synthetic, uncapped RNA and DNA primers of various lengths and sequences were hybridized with the DNA template and extended with Sequenase® and a-$^{32}$P-dGTP. When the reaction is carried out at 0° C. the only primers that give efficient extension are the 13 nt AlMV RNA and the corresponding sequence in DNA. Although incompletely extended products are visible on the gel, the reaction conditions have been optimized such that the most intense band corresponds to complete primer extension. A fainter band above the most intense band corresponds to a single base addition. Several DNA polymerases are known to catalyze the addition of a single base onto the 3'-OH termini of a blunt-ended DNA (Clark, 1988 Nucl. Acids Res. 16:9677–9686); presumably, a similar activity is also present in Sequenase®. The much less intense bands in the lane containing 14 nt RNA primer are attributable to a small contaminant of the 13 nt RNA present in the 14 nt ribonucleotide. No extension products are observed using either the full length 19 nt primer, AlMV primers smaller than 13 nt, or a heterologous 13 nt RNA derived from the 5' end of the b-globin transcript (5'-ACACUUGCUUUUG-3') (SEQ.ID. NO.:2). The Sequenase® reaction selectively extends the AlMV 13 nt primers and discriminates against sequences corresponding to uncleaved AlMV substrate or shorter nonspecific cleavage products. It is noteworthy that the high fidelity of Sequenase® prevents incorrect extension of AlMV primers differing in length by as little as a single base.

Figure 3:
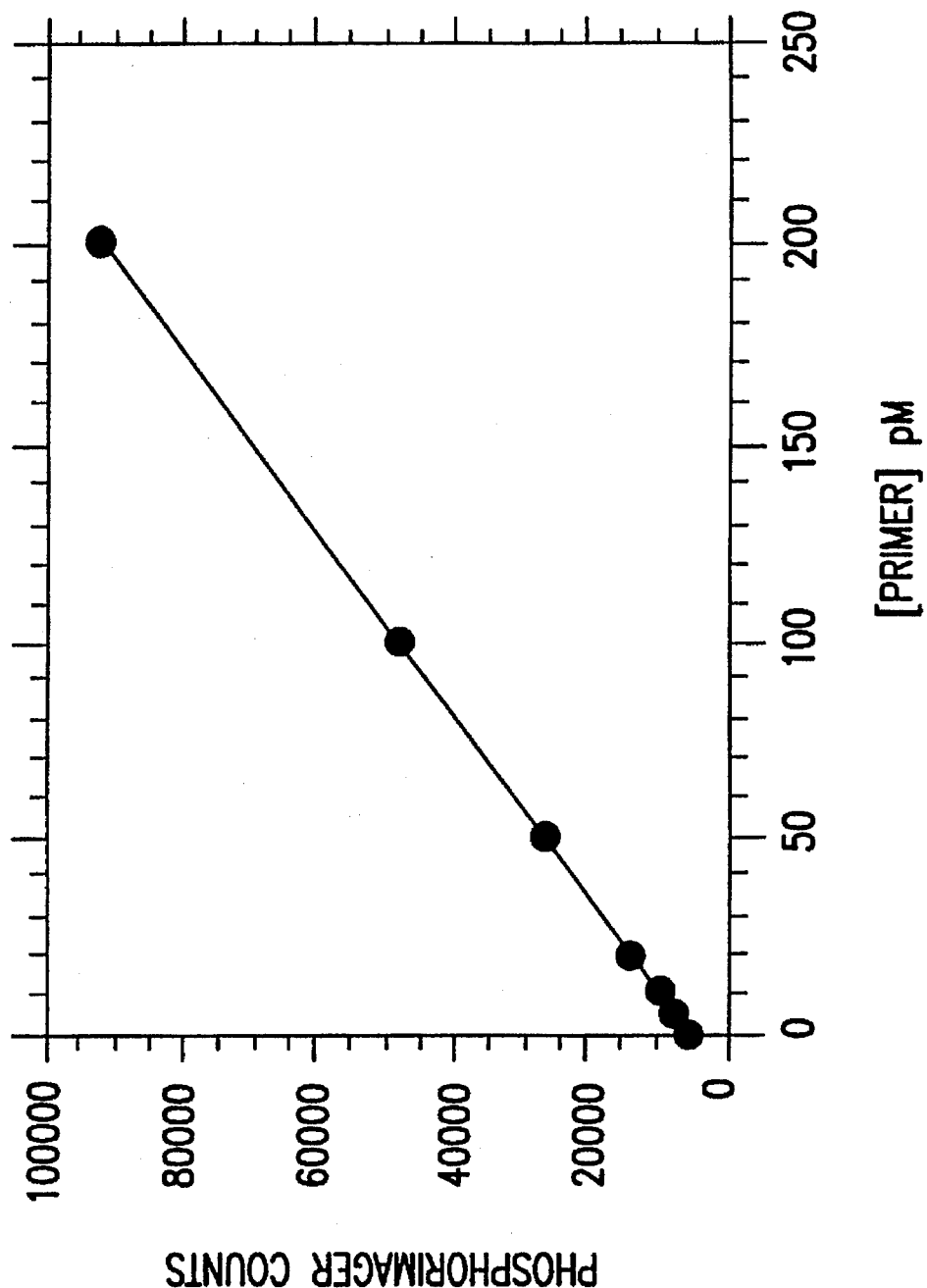
FIG. 3 is a graph demonstrating the linear response of DNA polymerase extension. Reactions were carried out as described in Example 1. The line drawn through the points is a linear least-squares fit to the data with a correlation coefficient of 0.9999.

It has been found in accordance with this invention that the polymerase extension reaction can be conveniently monitored by filtration through nylon membranes. Under the conditions described, quantitative binding of the extended product can be observed, with only a small amount (less than 0.0003%) of the unincorporated a-$^{32}$P-dGTP being retained on the nylon membrane. For high volume screening purposes, the filtration process can be performed using a 96-well manifold and the filter-bound radioactivity can be quantitated with either a phosphorimager device or a microplate scintillation counter. FIG. 3 shows the sensitivity and linear response using nylon membrane filtration and phosphorimager detection for extension of the 13 nt AlMV RNA primer. Excellent linearity is observed up to 200 pM primer in a reaction volume of 20 ul. Note that under typical assay conditions approximately 10% of the substrate will be converted to hybrid polymerase extension reaction product, corresponding to 40 pM of product; this amount is well within the linearity range and detection limits of the assay.

A background primer-independent reaction is observed which is manifest as a faint band running above the major extension products across all lanes in FIG. 2 and as a nonzero y-intercept in FIG. 3. In the absence of template, the former background signal is absent and the latter is dramatically reduced, suggesting that they are correlated. The background signals are independent of the presence of influenza core protein but they are dependent on Sequenase®. Thus, the background is due to a Sequenase®-catalyzed addition of a-$^{32}$p dGTP to the single-stranded template. Much higher background signals are observed using a template in which the 3'-OH group is not blocked by an aminolinker moiety, suggesting that the reaction requires a free 3'-OH. The background signals can be further reduced by treatment of the aminolinker-blocked template with ddATP and terminal deoxynucleotidyl transferase, which suggests that presence of a free 3'-OH containing impurity in the template.

Figure 4:
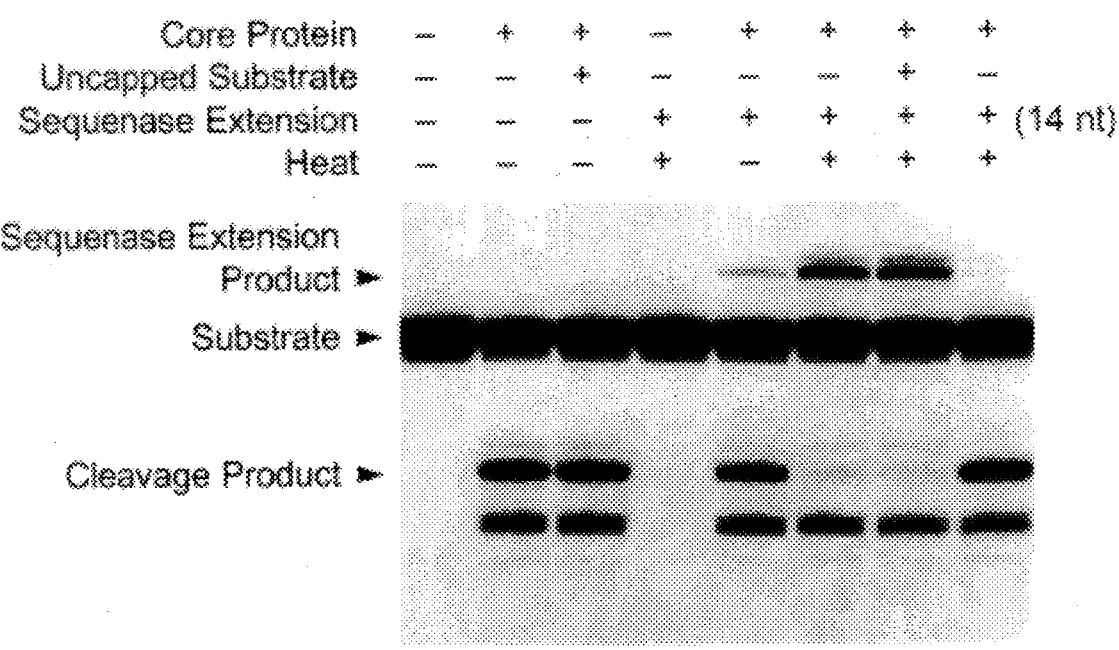
FIG. 4 is a gel demonstrating polymerase-catalyzed extension of the influenza endonuclease cleavage product, as described in Example 1.

In order to clearly characterize the coupled influenza endonuclease/polymerase extension process, a series of reactions were carried out using m$^7$G$^{32}$p- labeled AlMV substrate and unlabeled dGTP and were analyzed by gel electrophoresis. FIG. 4 shows that in the absence of core protein the AlMV substrate migrates as a single band corresponding to a length of 19 nt. Incubation of substrate with influenza core protein results in a major cleavage product as well as minor products that are shorter. The major product corresponds to cleavage at A13; this product is extended upon incubation with GTP. Similar results have previously been reported using the full-length AlMV RNA 4 (Plotch et al, 1989 Cell 23:847–858). The addition of a 10-fold excess of unlabeled, uncapped AlMV substrate does not affect the extent of cleavage. Incubation of substrate with polymerase, template and dGTP does not result in any extension in the absence of core protein. Cleavage of substrate by core protein following by polymerase extension results in the appearance of a faint band above the substrate band. This band corresponds to the addition of 10 dG residues to the 13 nt product. Note that in this sample the bulk of the cleavage product is not extended by polymerase. In contrast, in the sample which is incubated at 80° C. for 1 minute following cleavage, near-quantitative extension is observed. The dissociation of the cleavage product is likely to be quite slow and the heating step may serve to release the bound product by denaturing the influenza endonuclease complex. A faint band observed above the polymerase extension product likely corresponds to addition of an extra dG residue to the blunt-ended extended primer/template duplex, as was observed in FIG. 2. As in the case of the cleavage reaction alone, the coupled assay is not affected by the presence of a 10-fold excess of unlabeled uncapped AlMV substrate. In the last lane, the 24 nt template that contains a 14 nt complementary region was added instead of the 13 nt complementary template. The specific cleavage product is not extended in this sample, which confirms that the major product corresponds to cleavage at A13 and not at A 14.

The DNA polymerase coupled assay was validated for detecting influenza endonuclease inhibitors by using the inhibitor, (4-[N-benzene-sulfonyl-3-(4-chlorobenzyl) piperidin-3-yl]-2,4-dioxobutanoic acid), which we have previously identified using the gel-based assay. This compound is similar to the 4-substituted 2,4-dioxobutanoic acids recently described as inhibitors of the influenza endonuclease (Tomassini et al, 1994 AntiMicrob. Agents Chemother. 38:2827–2837). Titrations of the inhibition of the endonuclease by this compound were performed using a gel based assay and the DNA polymerase coupled assay of this invention under the same experimental conditions. The IC$_{50}$ values determined by fitting the data obtained over a range of 3 nM to 10 mM to a simple hyperbolic inhibition model are 260±60 nM for the gel assay and 220±50 nM for the DNA polymerase coupled assay. Within error, the potency of this compound is the same in both assays, indicating that the DNA polymerase coupled assay accurately monitors inhibition of the influenza endonuclease.

In another aspect of this invention, the DNA polymerase coupled assay provides a convenient method to determine the cleavage position of capped substrates. In the past, the site of cleavage by the influenza endonuclease was determined by generating sequence ladders with alkaline digestion or by digestion with RNAases and electrophoresis. The former method suffers from ambiguities arising from lability of the m7G residue in the cap structure to alkaline hydrolysis and the latter from the faster electrophoretic mobility of the 3'-phosphorylated sequences generated by RNases relative to the unphosphorylated 3'-OH ends generated by the influenza endonuclease. In contrast, the cleavage site can be unambiguously defined using the DNA polymerase coupled assay of this invention by comparing the extension reactions catalyzed using templates with complementary regions corresponding to the expected cleavage products. FIG. 4 illustrates this aspect of the invention, where the template with a 13 nt complementary region serves as a substrate, whereas the 14 nt complementary template does not.

Another major advantage of the coupled assay of this invention over existing methodologies is that the oligonucleotide product of interest can be detected in the presence of other sequences provided that they do not serve to prime polymerization. Thus, precise measurements of the reaction of interest can be performed even in complex, impure preparations.

The following non-limiting Examples are presented to better illustrate the invention.

EXAMPLES

General Experimental Methods

Oligo-deoxyribonucleotides and uncapped oligoribonucleotides were synthesized by Midland Certified Reagent Company (Midland, Tex.) and were purified by anion-exchange HPLC. Triphosphorylated oligonucleotides were synthesized and capped as described in co-pending patent application U.S. Ser. No. 08/480,068, (Attorney Docket No. 19406, filed herewith) which is hereby incorporated by reference. The sequence of the 19 nt substrate oligo-ribonucleotide is 5'-GUUUUUAUUUUUA-AUUUUC-3' (SEQ.ID. NO.:1). 3'-Truncated ribonucleotides were also synthesized which correspond to the 5'-region of the substrate with lengths of 14, 13, 12, 10 and 6 nt. Unless otherwise indicated, a 23 nt template was used in all experiments with the sequence: 5'-Biotin-CCCCCCCCCCTAAAAATAAAAAC-amino-3' (SEQ.ID.NO.:4), where the 5'-biotin is N-biotinyl-6-aminohexyloxyphosphoryl moiety and the 3'-amino is 3-amino-2-hydroxy)propoxy-phosphoryl. For some experiments a 24 nt template was used with the sequence: 5'-Biotin-CCCCCCCCCCTTAAAAATA-AAAAC-amino-3' (SEQ.ID.NO.:5). a-$^{32}$P-dGTP (3000 Ci/mmole) was obtained from Dupont NEN. Unlabeled dGTP was obtained from Pharmacia. Sequenase® Version 2.0 was obtained from United States Biochemicals (Cleveland, Ohio).

Unless otherwise noted, the polymerase extension reactions contained 1 nM primer, 50 nM template, 500 nM Sequenase®, and 500 nM dGTP and were carried out for 2 hours at the indicated temperature. The reactions were analyzed on 20% polyacrylamide 8M urea gels.

EXAMPLE 1

Cleavage Reactions and DNA Polymerase Reactions

Influenza cleavage reactions were performed at 25° C. in a buffer containing 100 mM tris[hydroxymethyl] aminomethane (Tris) pH 8.0, 50 mM KCl, 0.25 mM MgCl$_2$, 5 mM dithiothreitol (DTT), 4% (v/v) dimethyl sulfoxide (DMSO), in DEPC treated water. Polymerase extension reactions were performed in the same buffer, except that the MgCl$_2$ concentration was increased to 10 mM and the DMSO concentration to 9%. 500 nM dGTP was employed in extension reactions using end-labeled primers and a mixture of 50 nM a-$^{32}$P-dGTP and 450 nM unlabeled dGTP was employed with unlabeled primers. Unless otherwise indicated, extension reactions were performed at 0° C. For the inhibition measurements, the compound (4-[N-benzenesulfonyl-3-(4-chlorobenzyl)piperidin-3-yl]-2,4-dioxobutanoic acid) was preincubated with influenza core protein for 10 min. The cleavage reactions were initiated by adding 0.4 nM of unlabeled (gel assay) or end-labeled (polymerase extension assay) substrate in a 15 ul volume reaction containing 0.75 ul influenza core protein and were run for 10 min at 25° C. For the polymerase extension assay, the extension reaction was carried out in a 20 ul volume containing 50 nM Sequenase®, 500 nM dGTP, 50 nM template for 18 h at 0° C.

Reactions were analyzed either by electrophoresis in 20% polyacrylamide gels containing 8M urea or by filtering through 0.2 mm pore Nytran® membranes in a 96-well manifold (Schleicher and Schuell, Keene, N.H.). For filtration, samples were diluted with 200 ul of 250 mM EDTA, pH 8.0 and 200 ul was loaded onto the membrane equilibrated in 5X SSC (0.75M NaCl, 75 mM sodium citrate, pH 7.0) and filtered immediately. Each well was washed five times with 200 ul of 5X SSC, and the filter was removed from the manifold washed 3 times in 100 mL of 5X SSC.

Gels were visualized and filters were quantitated using a Phosphorimager® (Molecular Dynamics, Sunnyvale, Calif.) with the Imagequant® software provided by the manufacturer. In some experiments, the Nytran® filters were also quantitated using a TopCount® (Packard Instruments, Meriden, Conn.) microplate scintillation counter using Flexifilter® kits and Microscint® O scintillation fluid.

---

What is claimed is:

1. A method detecting the influenza endonuclease activity of a sample comprising:
   A) adding an influenza endonuclease substrate to a sample whose influenza endonuclease activity is to be assayed, to generate an RNA product;
   B) hybridizing the RNA product with a DNA template, said DNA template comprising a first segment substantially complementary to the RNA product and a 5'-extension region, which is attached to the 5'-end of the first segment, said extension region comprising at least one nucleotide, under hybridization conditions to form an RNA:DNA heteroduplex;
   C) adding labeled mononucleotide which is complementary to the second segment of the DNA template;
   D) adding a DNA polymerase to the heteroduplex structure under conditions permitting the DNA polymerase to catalyze the addition of the labeled mononucleotide to the 3'-end of the RNA product, to produce a labeled hybrid polymerase product; and
   E) measuring the amount of labeled hybrid polymerase product as a measure of the amount of influenza endonuclease activity of the sample.

2. A method according to claim 1 wherein the extension region of the DNA template comprises nucleotides not present in the first segment of the DNA template.

3. A method according to claim 2 wherein the extension region of the DNA template comprises substantially repeated nucleotides.

4. A method according to claim 3 wherein the extension region is at least 10 nucleotides in length.

5. A method according to claim 1 wherein the influenza endonuclease substrate is derived from the 5' end of Alfalfa Mosaic Virus 4 RNA.

6. A method according to claim 5 wherein the substrate is (SEQ.ID.NO.:1).

7. A method according to claim 4 wherein the second segment of the DNA template comprises a poly-C residue.

8. A method according to claim 1 wherein the labeled mononucleotides are radiolabeled.

9. A method according to claim 1 wherein the amount of labeled hybrid polymerase product is measured by passing the sample comprising labeled hybrid polymerase product and excess labeled mononucleotide through a filter, so that the labeled hybrid polymerase product is captured in the filter, and measuring the amount of label present on the filter.

10. A method according to claim 9 wherein the filter is a nylon filter.

11. A method according to claim 10 wherein the label is a radiolabel.

12. A method according to claim 1 wherein the sample to be assayed contains a putative inhibitor of influenza endonuclease activity.

13. A method according to claim 12, further comprising comparing the amount of influenza endonuclease activity of the sample to an activity determined for a control sample comprising influenza endonuclease which is not in the presence of a putative inhibitor.

14. A method of detecting the influenza endo-nuclease activity of a sample comprising:
   A) adding a 5' capped 19 nucleotide influenza endonuclease substrate derived from the 5'-end of Alfalfa Mosaic Virus RNA to a sample putatively containing an influenza endonuclease inhibitor whose activity is to be assayed, to generate a 13 nucleotide RNA product;
   B) hybridizing the 13 nucleotide RNA product with a DNA template, said DNA template comprising a first 3'-segment substantially complementary to the 13 nucleotide RNA product and a 5'-extension region, which is attached to the 5'-end of the first segment, said extension region comprising at least 10 nucleotides which are not present in the first segment, under hybridization conditions to form a RNA:DNA heteroduplex structure;
   C) adding labeled mononucleotide;
   D) adding a DNA polymerase to the heteroduplex under conditions permitting the DNA polymerase to catalyze the addition of the labeled mononucleotide to the 3'-end of the RNA product, to produce a radiolabeled hybrid polymerase product; and
   E) filtering the sample comprising the labeled hybrid polymerase product and excess labeled mononucleotide by passing the sample through a nylon filter so that the radiolabeled hybrid polymerase product is trapped by the filter; and
   F) measuring the amount of labeled hybrid polymerase product trapped on the filter and comparing that amount to that obtained when no putative influenza endonuclease inhibitor is present in a control sample.

15. A method according to claim 14 wherein the extension region of the DNA template comprises at least 10 substantially repeated cytosine nucleotides.

16. A method according to claim 15 wherein the labeled nucleotide is radiolabeled dGTP.

17. A method according to claim 1 wherein the RNA substrate is made by treating a 19 nt RNA containing a 5'-triphosphate with a guanylyltransferase.

18. A method according to claim 1 wherein the 3'-OH of the template is blocked with a (3-amino-2-hydroxy)-propoxyphosphoryl moiety.

19. A method according to claim 1 wherein the 3'-OH of the template is blocked by the introduction of a 3'-3'-A-5' linkage.

20. A method according to claim 1 wherein the DNA polymerase employed is Sequenase® Version 2, a mutant of bacteriophage T7 DNA polymerase, in which the 3' to 5' exonuclease activity is abolished by in vitro mutagenesis.

21. A method according to claim 1 wherein the polymerase extension reaction is carried out at least 10° C. below the melting temperature of the DNA:RNA complex.

22. A method of detecting the influenza endonuclease activity of a sample comprising:
   A) adding an influenza endonuclease substrate to a sample whose influenza endonuclease activity is to be assayed, to generate an RNA product;
   B) hybridizing the RNA product with a DNA template, said DNA template comprising a first segment complementary to the RNA product and a 5'-extension region, which is attached to the 5'-end of the first segment, said extension region comprising at least one nucleotide, under hybridization conditions to form an RNA:DNA heteroduplex;
   C) adding labeled mononucleotide which is complementary to the second segment of the DNA template;
   D) adding a DNA polymerase to the heteroduplex structure under conditions permitting the DNA polymerase to catalyze the addition of the labeled mononucleotide to the 3'-end of the RNA product; and
   E) measuring the amount of labeled hybrid polymerase product as a measure of the amount of influenza endonuclease activity of the sample,
   wherein the extension region of the DNA template comprises nucleotides not present in the first segment of the DNA template.

23. A method according to claim 22 wherein the extension region of the DNA template comprises substantially repeated nucleotides.

24. A method according to claim 23 wherein the extension region is at least 10 nucleotides in length.

25. A method according to claim 24 wherein the second segment of the DNA template comprises a poly-C residue.

* * * * *